US012023655B2

(12) United States Patent
Sofranko

(10) Patent No.: US 12,023,655 B2
(45) Date of Patent: Jul. 2, 2024

(54) OXIDES OF SULFUR AND THEIR USE AS OXYGEN TRANSFER REAGENTS

(71) Applicant: EcoCatalytic Inc., Weston, MA (US)

(72) Inventor: John A. Sofranko, Weston, MA (US)

(73) Assignee: Ecocatalytic Inc., Weston, MA (US)

( * ) Notice: Subject to any disclaimer, the term of this patent is extended or adjusted under 35 U.S.C. 154(b) by 0 days.

(21) Appl. No.: 18/108,810

(22) Filed: Feb. 13, 2023

(65) Prior Publication Data

US 2023/0271170 A1 Aug. 31, 2023

Related U.S. Application Data

(60) Provisional application No. 63/314,538, filed on Feb. 28, 2022.

(51) Int. Cl.

| | |
|---|---|
| ***C07C 5/48*** | (2006.01) |
| ***B01J 8/18*** | (2006.01) |
| ***B01J 8/26*** | (2006.01) |
| ***B01J 21/08*** | (2006.01) |
| ***B01J 23/34*** | (2006.01) |
| ***B01J 27/055*** | (2006.01) |
| ***B01J 27/25*** | (2006.01) |
| ***B01J 29/08*** | (2006.01) |
| ***B01J 37/02*** | (2006.01) |
| ***B01J 37/08*** | (2006.01) |

(52) U.S. Cl.

CPC ........... *B01J 27/055* (2013.01); *B01J 8/1827* (2013.01); *B01J 8/26* (2013.01); *B01J 21/08* (2013.01); *B01J 23/34* (2013.01); *B01J 27/25* (2013.01); *B01J 29/084* (2013.01); *B01J 37/0213* (2013.01); *B01J 37/08* (2013.01); *C07C 5/48* (2013.01); *C07C 2521/08* (2013.01); *C07C 2523/34* (2013.01); *C07C 2527/055* (2013.01); *C07C 2527/25* (2013.01); *C07C 2529/08* (2013.01)

(58) Field of Classification Search

CPC ...... B01J 29/7038; B01J 29/084; B01J 29/40; B01J 8/26; B01J 8/1827; B01J 27/02; B01J 27/053; B01J 27/055; C07C 5/48; C07C 2527/00; C07C 2529/08; C07C 2529/40; C07C 2529/70

USPC ........ 585/654, 656, 658; 502/216, 217, 218, 502/219, 220, 221

See application file for complete search history.

(56) References Cited

U.S. PATENT DOCUMENTS 10,138,182 B2 * 11/2018 Sofranko ............. B01J 37/0036
10,919,027 B1 2/2021 Sofranko et al.
11,104,625 B1 8/2021 Sofranko

FOREIGN PATENT DOCUMENTS

WO WO 2018/005456 * 1/2018

OTHER PUBLICATIONS

Ismall, "Fluid Catalytic Cracking (FCC) Catalyst Optimization to Cope with High Rare Earth Oxide Price Environment", BASF Chemical Company, 2011, 12 pages.

* cited by examiner

*Primary Examiner* — Elizabeth D Wood

(74) *Attorney, Agent, or Firm* — Buchanan, Ingersoll & Rooney PC

(57) ABSTRACT

An oxide of sulfur oxygen transfer reagent is provided. A method of producing olefins from hydrocarbons with a concomitant production of water (oxidative dehydrogenation), using the oxide of sulfur oxygen transfer reagent is also provided. The sulfur oxygen transfer reagent can be used as an oxygen transfer reagent, and therefore acts as a non-metal carrier, for oxygen in a redox looping reactor for an oxidative dehydrogenation process such as the conversion of ethane to ethylene. The reduced forms of oxides of sulfur, formed in in this oxidative dehydrogenation process, can be re-oxidized with air and generate useful process heat. Also provided are methods of using the oxide of sulfur oxygen transfer reagent, and an apparatus for effecting the oxidative dehydrogenation of the hydrocarbon feed. Methods of producing the oxide of sulfur oxygen transfer reagent are also provided.

24 Claims, 5 Drawing Sheets

OXIDES OF SULFUR AND THEIR USE AS OXYGEN TRANSFER REAGENTS

CROSS REFERENCE TO RELATED APPLICATIONS

This is a U.S. Non-Provisional Application claiming the priority of U.S. Provisional Application No. 63/314,538, filed Feb. 28, 2022, the entire contents of which are incorporated herein for all purposes.

TECHNICAL FIELD

The present disclosure relates to the use of oxides of sulfur in the dehydrogenation of hydrocarbons and the oxidative dehydrogenation (ODH) of ethane and higher hydrocarbons.

BACKGROUND

The oxidative dehydrogenation (ODH) of ethane, propane and other higher hydrocarbons are reactions of significant commercial value. These conversions may be done either catalytically by feeding a hydrocarbon and an oxygen containing gas, or in a redox oxygen transfer mode whereby an oxygen transfer reagent (OTA) supplies the necessary oxygen for the formation of water. Either system is exemplified by equation (1).

$$zC_nH_{2n+2-2\beta}+(z-1+\delta)\text{“O”}\rightarrow C_{(z\times n)}H_{2(z\times n)+2-2\beta-2\delta}+(z-1\pm\delta)H_2O \quad (1)$$

where: z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, “O” in equation (1) may be supplied by the reduction of a metal oxide or via the catalytic use of molecular oxygen. The reagent that supplies the oxygen is referred to herein as an oxygen transfer reagent (OTA).

Since most ODH reactions are quite exothermic, a preferred reactor system for these transformations are moving or fluid beds. A commercially viable catalyst or oxygen transfer reagent (OTA) will not only promote high conversion of the feeds to high selectivities of the desired products, thereby minimizing unwanted COx and coke products, but the OTA should preferably have the proper physical properties to be used these reactors. These desirable physical properties include:

- an ability to maintain fluidization at reaction temperatures; e.g. not be prone to agglomeration or excessive attrition at high temperature and thus maintain a free flowing mixture of gas and solid at reaction temperature;
- good physical strength and low attrition under fluidization conditions and be able to maintain these properties over many of redox (or chemical looping) cycles;
- an ability to maintain the desired reaction conversion rate and selectivity to the desired products for at least one month;
- an absence of highly toxic materials, or of materials having a geometry that may cause asbestosis;
- suitability for use in in a circulating fluid bed reactor;
- ability to selectively oxidatively dehydrogenate hydrocarbons, without taking the reaction all the way to complete combustion;
- operate at temperatures below 1100° C.;

- high oxygen carrying capabilities, thus allowing for more commercially viable OTA circulation rates than with OTA of low oxygen capacity; and
- resistance to deactivation and loss of product selectivity when exposed to common natural gas poisons such as hydrogen sulfide, carbon dioxide, water, and the like.

In addition to these desirable physical properties, the oxygen transfer reagent should preferably also be inexpensive to manufacture on a large scale and comparable in cost to commercially available fluid catalysts such as, for example, fluid catalytic cracking (FCC) catalysts.

There remains a need for such OTA systems that are selective for both oxidative coupling of methane (OCM) and the oxidative dehydrogenation (ODH) of ethane and higher hydrocarbons, are robust in the challenging conditions in fluidized bed reactors and at the same time are cost-effective to manufacture.

SUMMARY

The inventor has discovered a method whereby oxides of sulfur, preferably in the form of water soluble sulfur salts are added to supports to form supported active and selective oxides of sulfur oxygen transfer reagents (OTAs) for equation (1). These oxides of sulfur oxygen transfer reagents are effective for oxidative dehydrogenation of hydrocarbons at reaction temperatures comparable to current practice for the non-oxidative, thermal cracking or dehydrogenation of hydrocarbons to olefins.

A method of oxidatively dehydrogenating a hydrocarbon feed to produce a dehydrogenated hydrocarbon product and water is provided. The method comprises:

a) contacting the hydrocarbon feed with an oxide of sulfur oxygen transfer reagent; and b) oxidatively dehydrogenating the hydrocarbon feed at reaction conditions to produce the dehydrogenated hydrocarbon product and the water, whereby the oxygen of the water is derived from the oxide of sulfur oxygen transfer reagent, and the oxide of sulfur oxygen transfer reagent is reduced to form a reduced sulfur oxygen transfer reagent An apparatus for producing a dehydrogenated hydrocarbon product by oxidative dehydrogenation of a hydrocarbon feed to produce the dehydrogenated hydrocarbon product and water is provided. The apparatus comprises at least one vessel configured and arranged for:

i) contacting the hydrocarbon feed with an oxide of sulfur oxygen transfer reagent; and ii) oxidatively dehydrogenating the hydrocarbon feed at reaction conditions to produce the dehydrogenated hydrocarbon product and the water, whereby the oxygen of the water is derived from the oxide of sulfur oxygen transfer reagent, and the oxide of sulfur oxygen transfer reagent is reduced to form a reduced sulfur oxygen transfer reagent.

Also provided is a method of producing a supported oxide of sulfur oxygen transfer reagent. The method comprises the steps of:

a) combining an oxide of sulfur in form of a sulfur salt with a solvent to form a solution; and b) impregnating a solid support with the solution to form the supported oxide of sulfur oxygen transfer reagent.

DETAILED DESCRIPTION OF CERTAIN EMBODIMENTS

Figure 1:
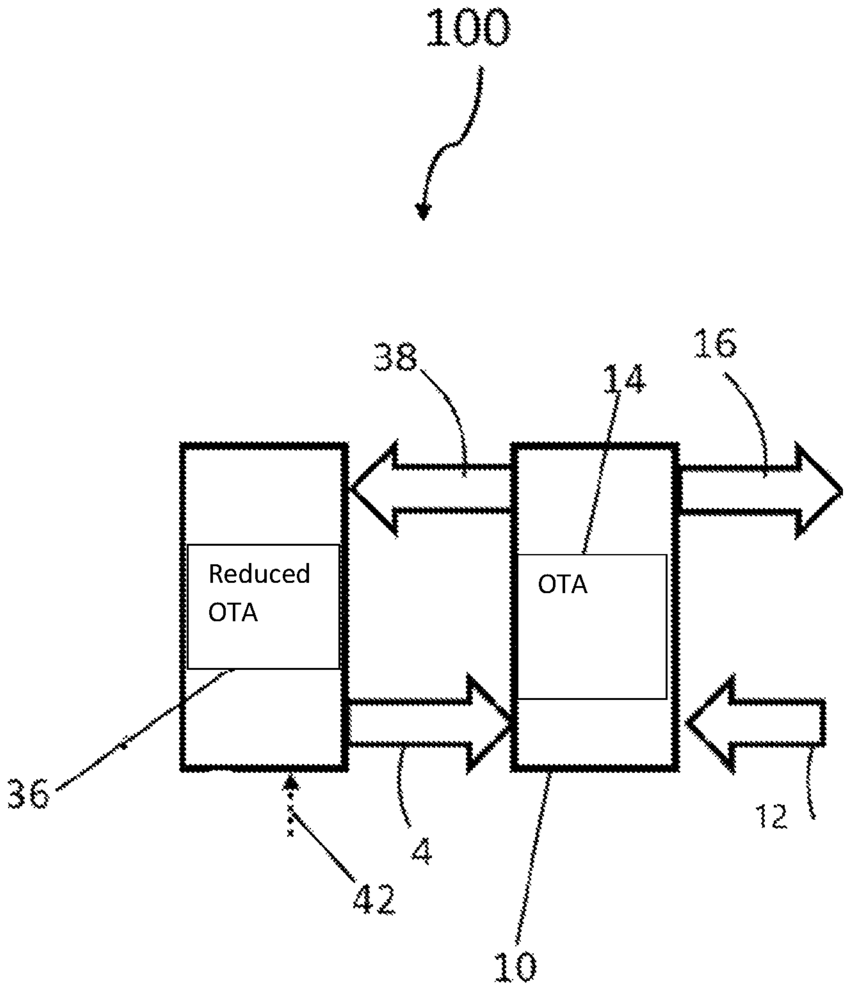
FIG. 1 shows an exemplary apparatus according to an embodiment of the invention.

As discussed briefly above, the oxidative dehydrogenation (ODH) of ethane and higher hydrocarbons are reactions of significant commercial value. Oxidative coupling of methane (OCM) is also of signification commercial value and may be done using the oxides of sulfur oxygen transfer reagents disclosed herein. These conversions may be done either catalytically by feeding a hydrocarbon and an oxygen containing gas, or in a redox oxygen transfer mode whereby an Oxygen Transfer reagent (OTA) supplies the necessary oxygen for the formation of water. Either reaction (OCM or ODH) is exemplified by equation (1), and will be referred to herein as either OCM or ODH; i.e. for the purposes of this disclosure, the terms, "coupling of methane" (OCM) and "oxidative dehydrogenation" (ODH) are considered to be interchangeable.

$$zCnH_{2n+2-2\beta}+(z-1+\delta)\text{"O"}\rightarrow C_{(z\times n)}H_{2(z\times n)+2-2\beta-2\delta}+(z-1+\delta)H_2O \quad (1)$$

where: z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in equation (1) may be supplied by the reduction of a metal oxide or via the catalytic use of molecular oxygen. The reagent that supplies the oxygen, whether a reducible metal oxide or another type of catalyst or catalyst system may be referred to herein as an oxygen transfer reagent (OTA).

According to some embodiments, the oxide of sulfur oxygen transfer reagent disclosed herein, when used in the oxidative dehydrogenation of a hydrocarbon feed in the presence of less than 1000 ppm weight of molecular oxygen, may undergo the following exemplary reactions:

$$CH_3CH_3+\text{Heat}\rightarrow CH_2CH_2+H_2$$

$$H_2+OTA^{ox}\rightarrow H_2O+OTA^{red}$$

$$OTA^{red}+\tfrac{1}{2}O_2\rightarrow OTA^{ox}\ \text{(re-oxidation)}$$

where $OTA^{ox}$ represents the oxidized form of the oxygen transfer reagent disclosed herein, and $OTA^{red}$ represent the reduced form of the oxygen transfer reagents disclosed herein.

A useful oxygen transfer reagent (OTA) will not only promote high conversion of the hydrocarbon feeds to high selectivities of the desired products, thereby minimizing unwanted COx and coke products, but the oxygen transfer reagent desirably has certain physical properties in order to be successfully used in these reactors.

These desirable physical properties include:

an ability to maintain fluidization at reaction temperatures; e.g. not be prone to agglomeration or excessive attrition at high temperature and thus maintain a free flowing mixture of gas and solid at reaction temperature;

good physical strength and low attrition under fluidization conditions and be able to maintain these properties over many of redox (or chemical looping) cycles;

an ability to maintain the desired reaction conversion rate and selectivity to the desired products for at least one month;

an absence of highly toxic materials, or of materials having a geometry that may cause asbestosis;

suitability for use in in a circulating fluid bed reactor; and resistance to deactivation and loss of product selectivity when exposed to common natural gas poisons such as hydrogen sulfide, carbon dioxide, water, and the like.

In addition to these desirable physical properties, the OTA should preferably also be inexpensive to manufacture on a large scale and comparable in cost to other commercial fluid catalysts such as, for example, fluid catalytic cracking (FCC) catalysts. It would be particularly beneficial if FCC type catalysts, either virgin or used and equilibrated, could be used as the support for the OTAs comprising oxides of sulfur of the subject invention. In particular, it is especially desirable if these OTAs can be produced using an incipient wetness impregnation method.

According to an embodiment, oxides of sulfur including an alkali metal as the counter ion to the oxide of sulfur, or oxides of sulfur including an alkaline earth as the counterion to the oxide of sulfur, such as sulfates or sulfites, when supported on a carrier material have one or more or all of these properties and are shown herein to be useful as oxygen transfer reagents for ODH systems, especially in fluidized bed reactors. These oxide of sulfur oxygen transfer reagents can be conveniently manufactured using an incipient wetness impregnation method.

According to another embodiment, commercially available FCC catalysts, based primarily on zeolite Y, are useful support materials for the subject invention. In general, OTAs were made and tested by simple incipient wetness impregnations of FCC and zeolite Y supports and, after calcination in air, produce OTAs for ODH with high selective ethylene, high oxygen carrying capacity and extremely good fluidization characteristics.

Oxide of Sulfur Oxygen Transfer Reagents:

It has been found that the oxygen transfer reagents of the present invention advantageously comprise an oxide of sulfur and a support material. The oxide of sulfur used may have an alkali metal or alkaline earth metal counter ion. These OTA materials may be impregnated, or ion exchanged, onto the support material.

The oxides of sulfur useful in the oxides of sulfur oxygen transfer reagent disclosed herein are compounds in which the average oxidation state of the oxides of sulfur may be from +2 to +6. The average oxidation state of the oxides of sulfur may be from +2, +3, +4, +5 or +6. The oxides of sulfur are typically in the form of sulfur salts of metals, also referred to herein as sulfur salts or sulfur metal salts. The average oxidation state of the oxide of sulfur in the oxide of sulfur oxygen transfer reagent may be +6. According to certain embodiments, the oxide of sulfur oxygen transfer reagent includes a compound that satisfies the formula $M_xSO_4$ where x is a number required to balance the negative formula charge of the $SO_4$ ion and M comprises at least one of alkaline metals, alkaline earth metals, actinide metals, lanthanide metals, trivalent transition metals, or combinations thereof. The sulfur oxygen transfer reagent may include a compound that satisfies the formula $M_xSO_y$ where x is a number required to balance the negative formula charge of the $SO_y$ ion, y is an integer from 1 to 6 and M comprises at least one of alkaline metals, alkaline earth metals, actinide metals, lanthanide metals, trivalent transition metals, or combinations thereof.

Non-limiting examples of suitable metal compounds of oxides of sulfur are $Li_2SO_4$, $Na_2SO_4$, $Na_2SO_3$, $CaSO_4$, $MgSO_4$, $FeSO_4$, $V(O)SO_4$, Particularly desirable are metal compounds of oxides of sulfur that are readily soluble in water. The following table shows the solubility of certain metal compounds of oxides of sulfur. As shown below, $CaSO_4$ is not especially soluble and therefore is less desirable.

| | Solubility in water wt. % | Temperature of solubility measurement |
|---|---|---|
| $Na_2SO_4$ | 28.1 | 25 |
| $Na_2SO_3$ | 27 | 20 |
| $CaSO_4$ | 0.26 | 25 |
| $MgSO_4$ | 35.1 | 20 |
| $FeSO_4$ | 29.5 | 25 |
| $V(O)SO_4$ | >25 | 20 |

It is useful to impregnate the oxide of sulfur oxygen transfer reagent on a high surface area support at loadings of great than 1 wt. %, preferably 5-30 wt. %. Therefore, high solubility of the sulfate salt in water (>10 g/100 cc of water) is needed using commonly practices method of incipient wetness.

Supports:

According to embodiments of the invention, the sulfur oxygen transfer reagent is supported on a solid support including at least one of a zeolite, silica, fluid catalyst cracking catalyst, spent fluid catalyst cracking catalyst, or a combination thereof. A particularly useful support is any commercial FCC catalyst including equilibrated or used catalysts that are destined for disposal.

According to an embodiment, the zeolite has a composition in accordance with the general formula: $M_2/nO\cdot Al_2O_3\cdot ySiO_2\cdot wH_2O$ where y is from 2 to 1,000,000, 000, M is a positively charged element for balancing the charge of the zeolite comprising at least one of protons, alkaline metals, or alkaline earth metals, n represents the valence of the positively charged element and w represents the number of water molecules per zeolite unit structure, such that, at least 5% of n are protons.

For example, the zeolite may have a composition in accordance with the above general formula where y is from 4 to 35. In one embodiment, the zeolite comprises ZSM-5, while in another embodiment the zeolite comprises at least one of sodium form of zeolite Y, ZSM-5, MCM 22, and MCM 56. Suitable amounts of Brönsted and/or Lewis acids may be utilized to optimize the activity of the zeolites. The molar ratio of the amount of oxides of sulfur together with their metal counterions to zeolite(s) may range from, e.g., 100:1 to 1:100; 95:5 to 5:95; 90:10 to 10:90; 85:15 to 15:85; 80:20 to 20:80; 75:25 to 25:75; 70:30 to 30:70; 65:35 to 35:65; 60:40 to 40:60; and/or 55:45 to 45:55. Additionally and/or alternatively, the molar ratio of the amount of oxides of sulfur and their metal counterions to zeolite(s) may range from 95:5 to 90:10; 90:10 to 85:15; 85:15 to 80:20; 80:20 to 75:25; 75:25 to 70:30; 70:30 to 65:35; 65:35 to 60:40; 60:40 to 55:45; 55:45 to 50:50; 50:50 to 45:55; 45:55 to 40:60; 40:60 to 35:65; 35:65 to 30:70; 30:70 to 25:75; 25:75 to 20:80; 20:80 to 15:85; 15:85 to 10:90; or 10:90 to 5:95.

Zeolite Y has been found to be a particularly useful support. However, other common zeolites, as known in the art, may be used. Other suitable zeolites as support materials in addition to zeolite Y are ZSM-5, MCM 22, MCM 56, mullite, mordenite, bentonite or a mixture thereof.

Particularly beneficial supports are compositions of zeolite Y as used in Fluid Catalytic Cracking (FCC) catalysts. FCC catalysts are often stabilized with rare earth and lanthanum metals, which gives them higher thermal stability. It has been discovered that these stabilized forms of FCC are most beneficial as supports for the oxides of sulfur OTAs. The stabilized FCC catalysts provide oxide of sulfur containing oxygen transfer reagents that give extended life activity after ODH cycles, in the redox ODH system. According to an embodiment of the invention, spent FCC catalysts or other catalysts that are destined for disposal are suitable as supports for the oxides of sulfur oxygen transfer reagents as disclosed herein.

According to an embodiment, the solid support comprises at least one of Sc, Y, La, Ce, Pr, Nd, Pm, Sm, Eu, Gd, Tb, Dy, Ho, Er, Tm, Yb, Lu or combinations thereof.

According to aspects of the invention, the supported oxide of sulfur oxygen transfer reagent comprises at least 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, 35 wt %, 36 wt %, 337 wt %, 8 wt %, 39 wt %, or 40 wt % of the dry weight of oxide of sulfur and the support. If the oxide of sulfur is in the form of a sulfur metal salt, as described above, the weight also includes the weight of the counterion for the oxide of sulfur. According to some embodiments the oxide of sulfur oxygen transfer reagent may comprise from 5 to 30 wt % of the sulfur salt, based on the total dry weight of the sulfur metal salt and the support.

Promoters:

The activity and selectivity to olefins using the OTAs of the subject invention can be enhance by promoting the OTA. According to some embodiments, the oxide of sulfur oxygen transfer reagent further comprises at least one promotor comprising at least one of alkali metals, alkaline earth metals, or mixtures thereof, wherein the promotor is not an oxide of sulfur. According to some embodiments the oxide of sulfur oxygen transfer reagent further comprises at least one promotor comprising at least one of Mn, Fe, Co, Cu, V, Nb, Ta, Cr, Mo, W, vanadium, or mixtures thereof.

According to some embodiments, the at least one promotor comprises at least one of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, or a mixture thereof.

As used here a promotor is understood to be a compound, composition or moiety that does not provide a reagent to produce the dehydrogenated hydrocarbon product and the water. In contrast, the role of the oxide of sulfur oxygen transfer reagent is understood to provide oxygen to the oxidative dehydrogenation of the hydrocarbon feed. The promotor serves to enhance the rate or selectivity of the oxidative dehydrogenation of the hydrocarbon feed without providing a reagent to the oxidative dehydrogenation reaction.

According to some embodiments, the oxide of sulfur oxygen transfer reagent does not include substantial amounts of mixed metal oxide materials or "MMO materials" meaning an oxide of one or more metals or metalloids from groups 1-15, or of the lanthanides or actinides of the periodic table. "Not include substantial amounts" means that the method utilized less than 5%, less than 4%, less than 1% or less than 0.5 wt % of such MMO materials, by weight of the oxide of sulfur oxygen transfer reagent and any MMO material (if any) present. According to another aspect of the invention, such MMO materials may be included in certain embodiments, as a physical mixture (rather than as a chemical compound) with the oxide of sulfur oxygen transfer reagents disclosed herein.

According to some embodiments, the oxide of sulfur oxygen transfer reagent does not include $CaSO_4$.

Methods of Oxidatively Dehydrogenating a Hydrocarbon Feed to Produce a Dehydrogenated Hydrocarbon Product and Water:

A method of oxidatively dehydrogenating a hydrocarbon feed is carried out by contacting the feed with an oxidation transfer reagent may proceed in the substantial absence of molecular oxygen or in the presence of molecular oxygen. In the former case, the oxidation transfer reagent as disclosed herein may itself provide the necessary oxygen, and thus may convert to a reduced form. In a separate step, this reduced form may be re-oxidized by the molecular oxygen.

A method of oxidatively dehydrogenating a hydrocarbon feed to produce a dehydrogenated hydrocarbon product and water is provided. The method comprises, the steps of:

a) contacting the hydrocarbon feed with an oxide of sulfur oxygen transfer reagent,
b) oxidatively dehydrogenating the hydrocarbon feed at reaction conditions to produce the dehydrogenated hydrocarbon product and the water, whereby the oxygen of the water is derived from the oxide of sulfur oxygen transfer reagent, and the oxide of sulfur oxygen transfer reagent is reduced to form a reduced sulfur oxygen transfer reagent.

According to an embodiment of the invention, the reduced sulfur oxygen transfer reagent comprises a sulfur moiety having an oxidation state of from 0 to +5.

According another embodiment, the reduced sulfur oxygen transfer reagent comprises a sulfur moiety having an oxidation state of from +2 to +5. According to an embodiment, the reduced sulfur oxygen transfer reagent comprises a sulfite, $SO_2$, $H_2S$ or elemental sulfur in any form.

According to an aspect of the invention, step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the oxygen in the oxide of sulfur oxygen transfer reagent.

According to another aspect of the invention, the step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen.

According to another aspect of the invention, step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

where: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the source of molecular oxygen.

According to another aspect of the invention step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

where z=2, n=1, β=0, and δ=0.

According to another aspect of the invention step b) oxidatively dehydrogenating the hydrocarbon feed proceeds according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O,$$

where z=1, n=2, β=0, and δ=1.

According to some embodiments, the step b) oxidatively dehydrogenating the hydrocarbon feed of the method may proceed according to the reaction:

$$zCnH_{2n+2-2\beta}+(z-1+\delta)\text{"O"}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and "O" is atomic oxygen; and wherein the atomic oxygen is supplied by the at least one oxygen transfer reagent. According to some embodiments, z=2, n=1, β=0, and δ=0. In particular this means that the reaction may comprise the oxidative coupling of methane to form ethylene. According to other embodiments, z=1, n=2, β=0, and δ=1. In particular, this means that the reaction may comprise the oxidative dehydrogenation of ethane to form ethylene. The oxidative dehydrogenation may comprise more than one reaction. Non-limiting examples of such multiple reactions may include: skeletal isomerization of olefins; oxidative dehydrogenation of methane to ethane and ethylene, and oxidative dehydrogenation of ethane to ethylene and higher olefins such as propylene and butylene.

According to some embodiments, the reaction conditions in step b) comprise the presence of essentially no molecular oxygen during the oxidative dehydrogenation of the hydrocarbon feed. In this embodiment, at least a portion of the oxide of sulfur oxygen transfer reagent may be reduced to produce a reduced sulfur oxygen transfer reagent. Without wishing to be bound by theory, this condition means that the oxygen needed for the oxidative dehydrogenation may be supplied by the oxide of sulfur oxygen transfer reagent. In particular, less than 5 wt %, less than 4 wt %, less than 3 wt %, less than 2 wt %, less than 1 wt %, less than 0.5 wt %, less than 1000 ppm weight, less than 500 ppm weight of molecular oxygen with respect to the total amount of the hydrocarbon feed, the oxide of sulfur oxygen transfer reagent and the molecular oxygen is present during the oxidative dehydrogenation step. Less than 1000 ppm weight of molecular oxygen is preferred. Non-limiting examples of sources of molecular oxygen are air, or molecular oxygen-containing streams resulting from other chemical processes.

According to some embodiments, the reaction conditions comprise the presence of less than 1000 ppm weight of molecular oxygen with respect to the total amount of the hydrocarbon feed, the oxide of sulfur oxygen transfer reagent and the molecular oxygen, and wherein at least a portion of the oxide of sulfur oxygen transfer reagent is reduced to produce a reduced sulfur oxygen transfer reagent. According to some embodiments, the reaction conditions comprise the presence of less than 900, 800, 700, 600, 500, 400, 300, 200, 100, 50, or less than 25 ppm weight of molecular oxygen with respect to the total amount of the hydrocarbon feed, the oxide of sulfur oxygen transfer reagent and the molecular oxygen, and at least a portion of the oxide of sulfur oxygen transfer reagent is reduced to produce a reduced sulfur oxygen transfer reagent.

According to other embodiments, the reaction conditions in step b) may comprise providing a source of molecular oxygen in an amount of greater than 1000 ppm weight of molecular oxygen during the oxidative dehydrogenation of the hydrocarbon feed. According to some embodiments, more than 1000 ppm weight, 2000 ppm weight, 3000 ppm weight, 0.5 wt %, 1 wt %, 5 wt %, 10 wt %, 12 wt %, 15 wt %, 20 wt %, 25 wt %, 30 wt % 35 wt %, 40 wt %, 45 wt %, 50 wt %, 55 wt % or up to 58.7 wt % of molecular oxygen with respect to the total amount of the hydrocarbon feed, the oxide of sulfur oxygen transfer reagent and the molecular oxygen may be supplied to the oxidative dehydrogenation step b).

According to some embodiments, the reaction conditions in step b) may comprise temperatures of from 700° C. to 1100° C. and at gas hourly space velocities (25° C. and 1 atmosphere) of 100 to 10,000 $hr^{-1}$. Other suitable temperatures may be from 300° C. to 1200° C., 350° C. to 1000° C., 400° C. to 1000° C., 400° C. to 800° C., 700° C. to 1100° C., 600-950° C., or from 500-900° C. or from 700-900° C. or from 800-850° C. According to embodiments of the invention, the reaction temperature may from 500° C. to 700° C. According to embodiments of the invention, the reaction temperature may be at least 600° C., 625° C., 650° C., 675° C., 700° C., 725° C., 750° C., 775° C., 800° C., 825° C., 850° C., 875° C., 900° C., 925° C., 950° C., 975° C., or at least 1000° C. According to certain embodiments the reaction temperature may be at most 1200° C., 1175° C., 1150° C., 1125° C., 1100° C., 1075° C., 1050° C., or at most 1025° C.

Pressure may be from sub-atmospheric to super-atmospheric with a range of 0.1 to 100 atm. In other embodiments, the pressure range may be 0.9 to 10 atm. Other pressure ranges may be from 0.9 to 1.5, 0.5 to 2, 0.9 to 5, 0.9 to 7, or 0.9 to 1.1 atm.

The gas hourly space velocity (25° C. and 1 atmosphere) may be from 100 to 10,000 $hr^{-1}$. The gas hourly space velocity may be from 2,400 to 4.00 $hr^{-1}$. The gas hourly space velocity may be at least 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, or at least 9500 $hr^{-1}$. The gas hourly space velocity may be at most 10,000, 9500, 9000, 8500, 8000, 7500, 7000, 6500, 6000, 5500, 5000, 4500, 4000, 3500, 3000, 2500, 2000, 1500, 1000, or at most 900 $hr^{-1}$.

According to some embodiments the method may further comprise, a step c) of contacting the at least one oxygen transfer reagent with a gas-phase promoter comprising at least one of gas phase water; steam; $CO_2$; halide gases; hydrogen halides such as HCl, HBr, and HF; and mixtures thereof. According to particular embodiments, the step c) may be performed at the same time as the step a).

According to another embodiment, the method may further comprise a step d) of contacting the oxide of sulfur oxygen transfer reagent with gas phase sulfur. According to an embodiment, the step d) may be performed at the same time as the step a). According to an embodiment, the gas comprising sulfur in d) may comprise at least one of $SO_3$, $SO_2$, $H_2S$, elemental sulfur in any form, or a mixture thereof. According to an embodiment, the gas comprising sulfur in d) may be a by-product of a hydrodesulfurization (HDS) unit.

According to some embodiments, the method of oxidatively dehydrogenating a hydrocarbon feed may further comprise steps e) removing a portion of the reduced oxygen transfer reagent; f) contacting the portion of the reduced sulfur oxygen transfer reagent with a gas comprising at least one of molecular oxygen, a compound comprising sulfur, or a combination thereof to produce a regenerated oxide of sulfur oxygen transfer reagent; and; and g) feeding the regenerated oxide of sulfur oxygen transfer reagent to step a).

According to an embodiment, the gas comprising sulfur in step f) comprises at least one of $SO_2$, $H_2S$, elemental sulfur in any form, or a mixture thereof. The sulfur preferably has an oxidation state of from −2 to 0. According to another embodiment, the gas comprising sulfur is a by-product of a hydrodesulfurization (HDS) unit.

The oxygen transfer reagents according to various embodiments of the present invention may be used in a chemical looping system to promote an ODH reaction via a Mars-van Krevelen-like mechanism. The effective utilization of the chemical looping mode of this invention may be performed in either fixed or circulating bed reactors. In the case of fixed bed reactors, multiple reactors may be used such that the oxidative dehydrogenation of the hydrocarbon feed and the re-oxidation of the oxygen transfer reagent are occurring continuously and in parallel as the hydrocarbon feed and the source of molecular oxygen (such as air) are alternately cycled between the reactor and a regeneration unit while the re-oxidation takes place.

According to an embodiment of the invention, the oxide of sulfur oxygen transfer reagent is in the form of a mixture with an additional oxygen transfer reagent different from the oxide of sulfur oxygen transfer reagent.

Apparatus for Producing a Dehydrogenated Hydrocarbon Product:

FIG. 1 shows a schematic of an apparatus 100 for producing a dehydrogenated hydrocarbon product in stream 16 by oxidative dehydrogenation of a hydrocarbon feed in stream 12 to produce the dehydrogenated hydrocarbon product and water. The apparatus 100 comprises:

a vessel 10 configured and arranged for:

i) contacting the hydrocarbon feed 12 with the oxide of sulfur oxygen transfer reagent 14 disclosed herein; and ii) oxidatively dehydrogenating the hydrocarbon feed 12 at reaction conditions to produce the dehydrogenated hydrocarbon product and the water in stream 16 and to convert a portion of the oxide of sulfur oxygen transfer reagent to a reduced sulfur oxygen transfer reagent 38.

According to some embodiments, the vessel 14 may be a reactor selected from a fluidized bed reactor, a moving bed reactor, or a shell and tube reactor. The vessel may further comprise an inlet and an outlet. The apparatus 100 may further comprise a regeneration unit 36 in communication with the inlet and the outlet. The regeneration unit may be constructed and arranged to:

iii) receive at least a portion of the reduced sulfur oxygen transfer reagent 38 from the outlet;
iv) contact the reduced sulfur oxygen transfer reagent 38 with a gas comprising at least one of molecular oxygen, a compound comprising sulfur, or a mixture thereof 42 to produce a regenerated oxide of sulfur oxygen transfer reagent 4; and
v) feed the regenerated oxide of sulfur oxygen transfer reagent 38 to the inlet.

The vessel 14 may be configured and arranged to contact the oxide of sulfur oxygen transfer reagent with gas phase sulfur.

In the instance where the conversions of (1) are run in a co-feed mode with a mixture of hydrocarbon feed 12 and the oxide of sulfur oxygen transfer reagent 38 are fed to the vessel 14 together, it is be useful to use reactors as vessel 14 that can effectively remove the heat of reaction, such as shell and tube reactors.

The oxygen transfer reagents according to various embodiments of the present invention may be used in a chemical looping system to promote an ODH reaction via a Mars-van Krevelen-like mechanism. The effective utilization of the chemical looping mode of this invention may be performed in either fixed or circulating bed reactors. In the case of fixed bed reactors, multiple reactors 14 and regeneration units 36 may be used such that hydrocarbon oxidation and the re-oxidation of the oxygen transfer reagent are occurring continuously as hydrocarbon feed 12 and the gaseous source of molecular oxygen and/or compound comprising sulfur 42, which may be or comprise air are alternately cycled to multiple reactors.

Hydrocarbon Feed:

Suitable hydrocarbon feeds for use in embodiments of the present invention may be selected from methane; ethane; propane; isomers of butane; isomers of butene, isomers of pentane; isomers of pentene; isomers of hexane; cyclohexane; isomers of hexene; cyclohexene; and mixtures thereof.

Method of Preparing the Support Oxide of Sulfur Oxygen Transfer Reagent:

A method of producing a supported oxide of sulfur oxygen transfer reagent is provided. The method generally is the incipient wetness impregnation method used for the preparation of heterogeneous catalysts. This method is attractive because of its technical simplicity, low costs and limited amount of waste. Generally, a support is impregnated with a precursor-containing solution and may then be dried. The impregnated support may then be calcined, either before or after drying. The solvent is preferably water. Other suitable include alcohols, especially ethanol or methanol or mixtures thereof with water.

The preparation method thus comprises the steps:

a) combining an oxide of sulfur in form of a sulfur salt with a solvent to form a solution;
b) impregnating a solid support with the solution to form the supported oxide of sulfur oxygen transfer reagent.

The method may further comprise c) calcining the supported oxide of sulfur oxygen transfer reagent in the presence of air.

The supported oxide of sulfur oxygen transfer reagent comprises at least 1 wt %, preferably, 5-30 wt % of the sulfur salt, based on the total dry weight of the sulfur salt and the support. Therefore, a high solubility of the oxide of sulfur salt in water (>10 g/100 cc of water) is desirable using the commonly practiced method of incipient wetness.

EXAMPLES

The following non-limiting examples are provided for the purpose of elucidating the advantages obtained from aspects of the present invention and are not intended to limit the invention to only these exemplary embodiments.

The sulfur oxygen transfer reagents were prepared from aqueous solutions of sulfate or nitrate salts by the method of incipient wetness impregnation on supports as shown in Table 1. The loading level of the alkali sulfate was 0.014 moles of sulfate per 10 g of support. 4 g of sodium sulfate was dissolved in 8 ml of distilled water. This solution was added to 10 g of FCC support, just until the solid has been wetted with the sulfate solution. After impregnation, this material was dried at 110° C. for approximately 16 hours and then calcined in air at 850° C. for 4 hours.

The oxidative hydrocarbon dehydrogenation reactions conversions were done in a cyclic redox mode such that ethane and air, or oxygen, were not present at the same time in the reactor. Nitrogen was used to purge after a 15 second pulse of ethane, and after a 10 minute regeneration of the reduced OTA. Products were collected with gas bags and analyzed by gas chromatography. Samples of the spent air from regeneration of the OTA showed minimal carbon oxide formation, and therefore indicate that very there was very little coke formation during the ethane cycle. The reactor used was a 0.75 inch ID high density alumina tube. For some experiments, as noted in the Examples, $SO_2$ and $H_2S$ were measured in the product stream using an RAE Q-RAE 3 gas monitor. In all Examples, 100% hydrogen selectivity is equivalent to the molar amount of hydrogen that would be formed by the stoichiometric conversion of ethane to hydrogen and ethylene. In addition, 100% water is the equivalent of the molar amount of water that would be formed if all the hydrogen produced is oxidized to water by the OTA. The results from these experiments are shown in Tables 2 and 3 and FIGS. 2, 4 and 5.

TABLE 1

| *OTA # | Description |
|---|---|
| 1 | Commercial Rare Earth stabilized FCC catalyst from Grace Chemical |
| 2 | OTA after calcination at 1,100° C. for 12 hr. |
| 3 | Zeolite Y, Si/Al = 30 |
| 4 | OTA #1 plus $Na_2SO_4$ |
| 5 | Silica Gel plus $Na_2SO_4$ |
| 6 | OTA #3 plus $Na_2SO_4$ |
| 7 | OTA #1 plus $NaNO_3$ |
| 8 | OTA #7 plus $SO_3$ |

*The OTA# correspond to the Examples below, e.g., OTA#1 was used in Comparative Example 1, OTA#4 was used in Inventive Example 4, etc.

TABLE 2

Results of Examples 1-8

| OTA/Catalyst | 1 | 2 | 3 | 4 | 5 | 6 | 7 | 8 |
|---|---|---|---|---|---|---|---|---|
| % $CH_3CH_3$ conversion | 81.1 | 79.4 | 79 | 78 | 80.8 | 65.2 | 81 | 82 |
| %*$C_{2+}$ selectivity | 82.7 | 90.0 | 83 | 88 | 84.8 | 91.3 | 90 | 78 |
| %$C_{2+}$ yield | 67.1 | 71.5 | 66 | 68 | 68.5 | 59.5 | 73 | 64 |
| % ethylene selectivity | 72.5 | 81.6 | 74 | 79 | 69.7 | 80.1 | 81 | 66 |
| % ethylene yield | 58.9 | 64.8 | 58 | 61 | 56.3 | 52.2 | 65 | 55 |
| % $CO_2$ selectivity | 1.6 | 0.2 | 1 | 3 | 7.0 | 1.3 | 0 | 13 |
| % CO selectivity | 4.4 | 1.6 | 3 | 2 | 2.2 | 2 | 2 | 5 |
| % $CO_2$ yield | 1.3 | 0.2 | 0 | 2 | 5.7 | 0.8 | 0 | 10 |
| % CO yield | 3.6 | 1.2 | 2 | 2 | 1.8 | 1.3 | 1 | 4 |
| % $H_2$ selectivity | 94.0 | 91.9 | 96 | 28 | 50.3 | 20.0 | 98 | 26 |
| % $H_2O$ selectivity | 6.0 | 8.1 | 4 | 72 | 49.7 | 80.0 | 2 | 74 |
| Run Temperature, ° C. | 827 | 823 | 825 | 825 | 827 | 826 | 825 | 825 |
| GHSV, $hr^{-1}$ | 2400 | 2400 | 2400 | 2400 | 2400 | 2400 | 2400 | 2400 |

*$C_{2+}$ is hydrocarbons having more than 2 carbon atoms

Example 1. (Comparative)

Using cyclic redox reaction mode conditions, 5 ml of a commercial rare earth stabilized FCC was charged to the reactor. The results shown in Table 2 as OTA/Catalyst #1 demonstrate that this material had little oxidative dehydrogenation capacity as demonstrated by high production of hydrogen and small amount of water produced. A small amount of oxidation was observed with $CO_2$ and CO as product.

Example 2. (Comparative)

A sample of commercial FCC catalyst from Example 1 was calcined at 1,100 C in air for 12 hours in order to convert the FCC zeolite Y to mullite (aluminum silicate). Using cyclic redox reaction mode conditions, 5 ml of this mullite material was charged to the reactor. The results shown in Table 2 as OTA/Catalyst #2 demonstrate that this material had little oxidative dehydrogenation capacity as evidenced by the high production of hydrogen and low amount of water produced. A small amount of oxidation was observed with $CO_2$ and CO as product which is a possible result of the presence of rare earth oxides in the FCC.

Example 3. (Comparative)

A 5 ml sample of zeolite Y (Si/Al=30) from Alfa-Aesar was charged to the redox reactor. The results for ethane conversion are shown as OTA/Catalyst #3 in Table 2. Like comparative examples 1 and 2, zeolite Y on its own had little oxidative dehydrogenation capacity as evidenced by the high production of hydrogen and low amount of water produced.

In summary, comparative Examples 1-3 demonstrate that both commercially available FCC catalyst and research grade zeolite Y have low capacity for the oxidative conversion of ethane to olefins and concomitant production of water. The small amount of $CO_2$ and CO produced was likely due to low contaminations of metals in these materials as sourced from the vendors.

Example 4. (Inventive)

To 10 g of the commercial FCC catalyst was added 2 g of $Na_2SO_4$ by using the impregnation methods as previously described to provide OTA #4. Ethane conversion runs, as shown in Table 2 as OTA #4, demonstrated significant activity for the conversion of ethane to olefins and the production of water, $CO_2$ and CO. These oxidation products at levels much higher than in Examples 1-3 clearly demonstrate that sulfate is acting as an OTA for this reaction. In addition, the ethane reactor effluent contained approximately 20-100 ppm each of $SO_2$ and $H_2S$ which are reduction products of sulfate.

Example 5. (Inventive)

To 10 g of silica gel (surface area 300 $m^2/g$) was added 2 g of $Na_2SO_4$ by using methods as previous described to provide OTA #5. Ethane conversion runs, as shown in Table 2 as OTA #5, demonstrated significant activity for the conversion of ethane to olefins and the production of water, $CO_2$ and CO. These oxidation products at levels much higher than in Examples 1-3 clearly demonstrate that sulfate is acting as an OTA for this reaction. In addition, the ethane reactor effluent contained approximately 50-180 ppm each of $SO_2$ and $H_2S$ which are reduction products of sulfate. However, compared with OTA #4, the silica OTA was less active for the conversion of hydrogen to water and also released a higher level of $SO_2$ and $H_2S$ during the ethane conversion than the sodium sulfate/FCC OTA #4. In summary, the silica gel was a surprisingly useful support for the oxide of sulfur as the oxygen transfer reagent, but did tend to release the oxide of sulfur over fewer cycles before requiring regeneration. 7 This example demonstrates that the oxide of sulfur needs to be impregnated on the support in order to be an effective source of oxygen. Trace amounts of the oxide of sulfur adsorbed on the silica need to be replaced.

Example 6. (Inventive)

Figure 2:
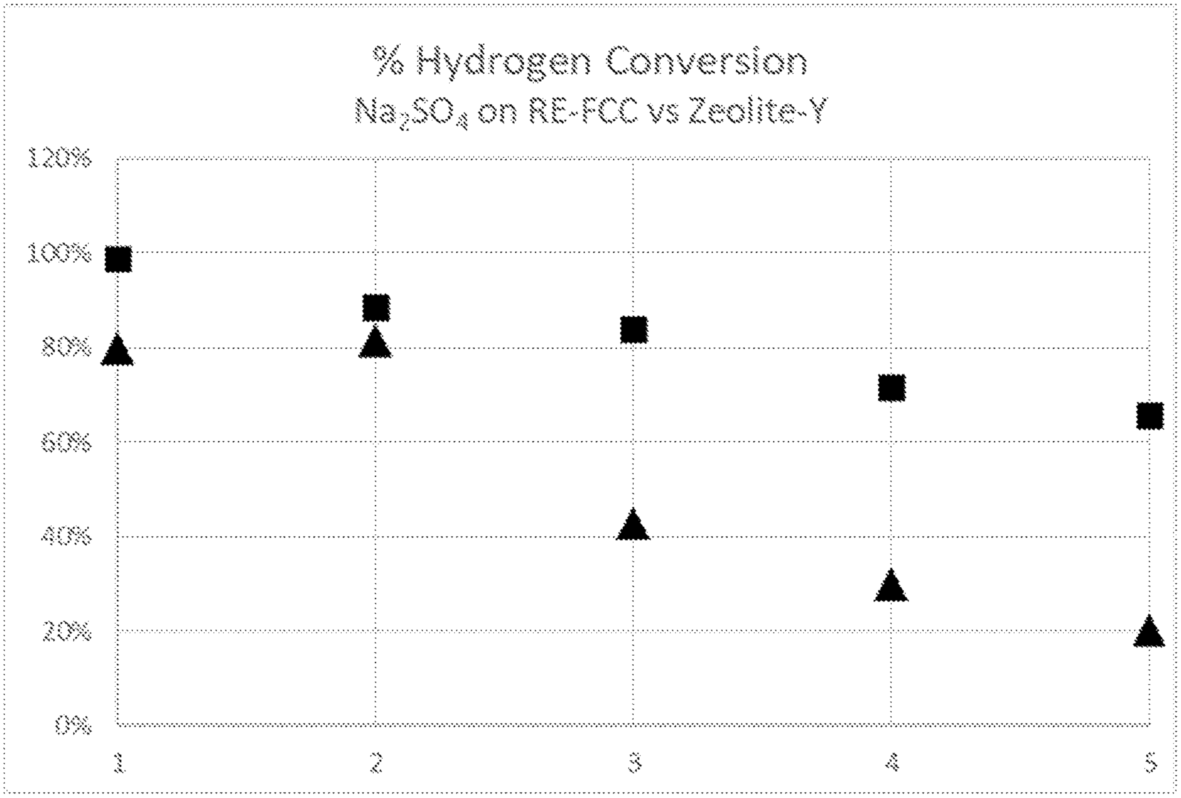
FIG. 2 compares the usefulness of commercial rare earth stabilized FCC catalyst (squares) as a support for the sulfate OTA to the usefulness of zeolite Y (triangles) as a support for the sulfate OTA.

To 10 g of zeolite Y, as in catalyst #3, (Si/Al=30) was added 2 g of $Na_2SO_4$ by using methods as previous described. Ethane conversion runs, as shown in Table 2 as OTA #6, demonstrated significant activity for the conversion of ethane to olefins and the production of water, $CO_2$ and CO. These oxidation products were at levels much higher than in Examples 1-3 and therefore clearly demonstrate that sulfate is acting as an OTA for this reaction. In addition, the ethane reactor effluent contained approximately 20-100 ppm each of $SO_2$ and $H_2S$ which are reduction products of sulfate. However, compared with OTA #4, the zeolite Y supported OTA lost its activity faster with redox cycles for the conversion of hydrogen to water than the sodium sulfate/FCC OTA #4. As shown in FIG. 2, the % hydrogen conversion for OTA #6 (triangles) falls off faster than for OTA #4 (squares).

Example 7. (Comparative)

10 g of the commercial FCC catalyst was 2.4 g of $NaNO_3$ impregnated, using the incipient wetness impregnation method as previously described. Ethane conversion runs, as shown in Table 2 as OTA #7, demonstrated significant activity for the conversion of ethane to olefins but very low production of water, $CO_2$ and CO, indicating that the impregnated FCC was not contributing oxygen to the reaction, i.e., was not acting as an oxygen transfer reagent. This OTA did demonstrate some oxidative dehydrogenation of ethane but at a lower level that OTA #1 or OTA #4. In addition, the $SO_2$ and $H_2S$ contained in the ethane reactor effluent was approximately 5-10 ppm and lower than observed with OTA #4. Therefore, these results indicate that commercial FCC, when impregnated with sodium nitrate, has a low level of ODH activity and is much lower than FCC that has been impregnated with $Na_2SO_4$, as shown in inventive example #4. This comparative example 7 demonstrates that oxygen of the oxide of sulfur is providing the oxygen as the oxygen transfer reagent.

Example 8. (Inventive)

Figure 3:
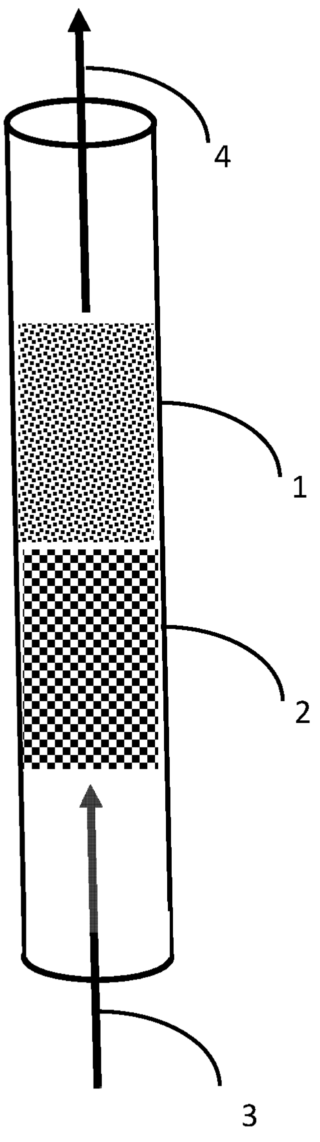
FIG. 3 shows an experimental apparatus designed to treat non-sulfate comprising OTAs with $SO_3$ gas as demonstrated in Example 8.
Figure 4:
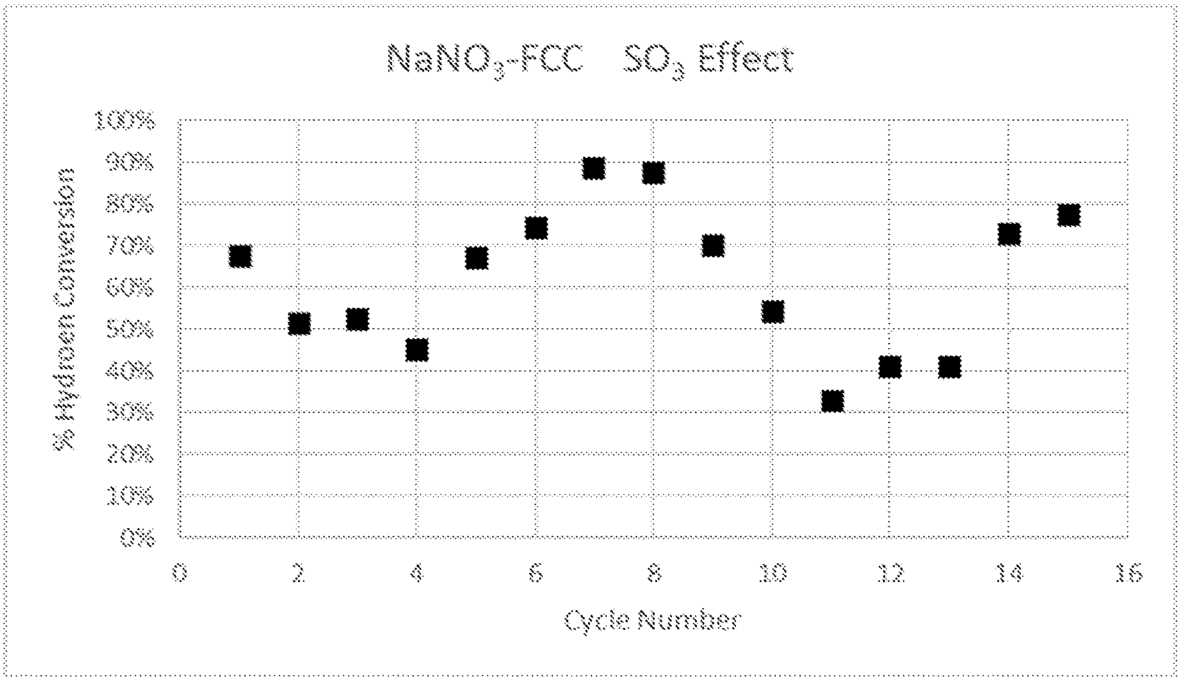
FIG. 4 shows the results for the conversion of hydrogen vs. run cycle without an $SO_3$ activation gas (runs 1-4), and in the presence of an $SO_3$ activation gas (runs 5-15)

The FCC impregnated with $NaNO_3$ on OTA #7, of Comparative Example 7, was charged to a reactor shown schematically in FIG. 3. In FIG. 3, 1 is the FCC impregnated with $NaNO_3$ on FCC OTA, # of Comparative Example 7. In addition, 5 g of sodium bisulfate 2 in FIG. 3 was loaded below the 5 ml charge of the OTA of Example 7 and separated from the OTA by a layer of alumina wool. The flow of all gases was from bottom 3 to top 4 as shown in FIG. 3. The results from Example 8 are shown in FIG. 4. In this plot, the % hydrogen conversion is plotted vs the run cycle. The % hydrogen conversion is a metric for the amount of oxidative dehydration, whereby high hydrogen conversion indicates high ODH as compared to thermal pyrolysis. The first four runs as shown in FIG. 4 are those using the $NaNO_3$ OTA #7 without the sodium bisulfate and demonstrate the baseline oxidative capacity for OTA of the comparative example 7, which decreases with each additional run cycle. Starting with run cycle 5 shown in FIG. 4 are the results from this Example 8, after the addition of the sodium bisulfate 2 into the reactor shown in FIG. 3. The temperature of sodium bisulfate zone 2 of the reactor was approximately 650° C. and the temperature of zone 3 was 825-827° C. No air was used at any time during these cycles. Sodium bisulfate is known to decompose to sodium sulfate, with the release of $SO_3$ gas, at this temperature. Starting in cycle 5, there was an increase in the conversion of hydrogen to water as the $SO_3$ gas (decomposition product of the sodium bisulfate) was introduced into the redox cycle. The hydrogen conversion activity increased from runs 5 through 7 and then declined in runs 8 through 11 as the sodium bisulfate was depleted. In all the runs, 5 through 11, there was no air brought into the system for regeneration. Starting at run 12, air was introduced to re-oxidize the OTA. The air introduction resulted in an immediate increase in hydrogen conversion and at cycle 15 was almost at the same level as the fresh OTA, before it had been cycled in the absence of air. This experiment demonstrates that the introduction of $SO_3$ gas to the comparative OTA #7 increased the oxidative capacity of the OTA for the conversion of hydrogen to water. In addition, this increase can occur in the absence of air as long as $SO_3$ gas is provided. This $SO_3$ treated OTA retains sulfur and can be reactivated by regeneration with air. The example demonstrates the effectiveness of $SO_3$ adsorbed onto the commercial FCC as an oxygen transfer reagent.

Figure 5:
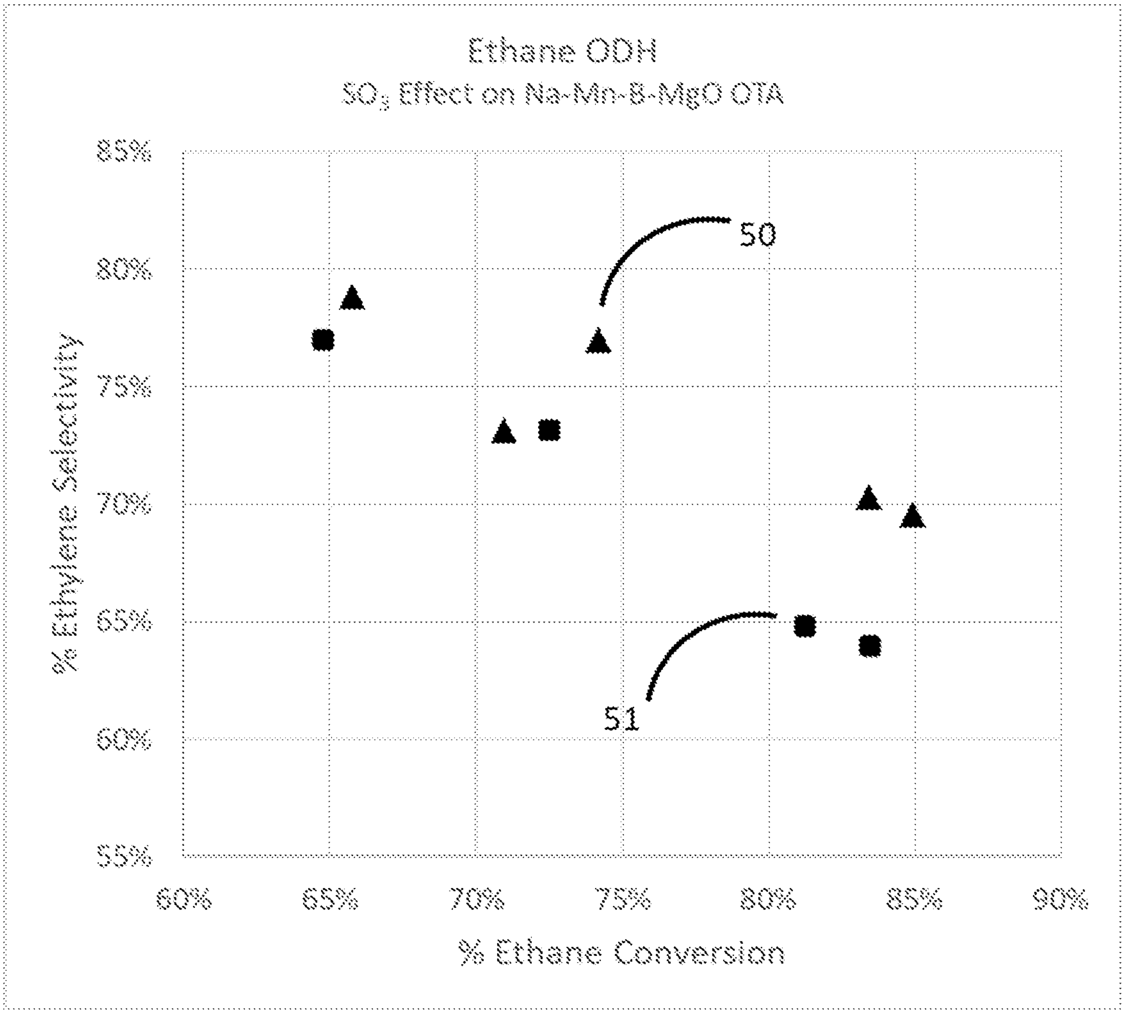
FIG. 5 shows the conversion of ethane vs. the selectivity to ethylene and the ability of the subject sulfate comprising OTA to improve the yield of ethylene when used as a physical mixture of other non-sulfate OTAs, as demonstrated in Example 9.

Example 9. (Invention) Physical Mixture of the Sodium Sulfate on FCC OTA with a Metal Oxide Oxygen Transfer Reagent A sample of a Na—Mn—B—MgO ethane OTA was made according to the methods of U.S. Pat. No. 10,919,027 B1, the entire contents of which are incorporated by reference herein for all purposes. To the alumina reactor was charged 4.5 g of this Na—Mn—B—MgO OTA and 0.5 g of the sodium sulfate on FCC OTA #4, of Example #4. The ODH results of this mixture (50-triangles) are compared to the ODH results with the pure Na—Mn—B—MgO (51-squares) sample as shown in FIG. 5. The addition of the $Na_2SO_4$/FCC OTA significantly improved the yield of olefins via the ethane ODH reaction. In addition, the mixture of the $Na_2SO_4$/FCC with the Na—Mn—B—MgO OTA maintained better fluidization at temperatures above 800° C. when compared to the Na—Mn—B—MgO OTA alone.

What is claimed is:

1. A method of oxidatively dehydrogenating a hydrocarbon feed to produce a dehydrogenated hydrocarbon product and water, the method comprising:

a) contacting the hydrocarbon feed with an oxide of sulfur oxygen transfer reagent, wherein the oxide of sulfur oxygen transfer reagent does not include substantial amounts of an oxide of one or more metals or metalloids from groups 1-15, or of the lanthanides or actinides, b) oxidatively dehydrogenating the hydrocarbon feed at reaction conditions to produce the dehydrogenated hydrocarbon product and the water, whereby the oxygen of the water is derived from the oxide of sulfur oxygen transfer reagent, and the oxide of sulfur oxygen transfer reagent is reduced to form a reduced sulfur oxygen transfer reagent, d) contacting the oxide of sulfur oxygen transfer reagent with gas phase sulfur.

2. The method of claim 1, wherein the average oxidation state of the oxide of sulfur is from +2 to +6.

3. The method of claim 1, wherein the average oxidation state of the oxide of sulfur is +6.

4. The method of claim 1, wherein the oxide of sulfur oxygen transfer reagent comprises a compound that satisfies the formula $M_xSO_4$ where x is a number required to balance the negative formula charge of the $SO_4$ ion and M comprises at least one of alkaline metals, alkaline earth metals, actinide metals, lanthanide metals, trivalent transition metals, or any combination thereof.

5. The method of claim 1, wherein the oxide of sulfur oxygen transfer reagent comprises a compound that satisfies the formula $M_xSO_y$ where x is a number required to balance the negative formula charge of the $SO_y$ ion, y is an integer from 1 to 6, and M comprises at least one of alkaline metals, alkaline earth metals, actinide metals, lanthanide metals, trivalent transition metals, or any combination thereof.

6. The method of claim 1, wherein the oxide of sulfur oxygen transfer reagent comprises at least one of $Li_2SO_4$, $Na_2SO_4$, $Na_2SO_3$, $CaSO_4$, $MgSO_4$, $FeSO_4$, $V(O)SO_4$, or any combination thereof.

7. The method of claim 1, wherein the oxide of sulfur oxygen transfer reagent is supported on a solid support comprising at least one of a zeolite, silica, spent fluid catalyst cracking catalyst, or any combination thereof.

8. The method of claim 7, wherein the solid support further comprises at least one of Sc, Y, La, Ce, Pr, Nd, Pm, Sm, Eu, Gd, Tb, Dy, Ho, Er, Tm, Yb, Lu, or any combination thereof.

9. The method of claim 7, wherein the zeolite has a composition in accordance with the general formula: $M_2/nO\cdot Al_2O_3\ ySiO_2\cdot wH_2O$ where y is from 2 to 1,000,000,000; M is a positively charged element for balancing the charge of the zeolite comprising at least one of protons, alkaline metals, or alkaline earth metals; n represents the valence of the positively charged element; and w represents the number of water molecules per zeolite unit structure, such that at least 5% of n are protons.

10. The method of claim 7, wherein the zeolite comprises at least one of zeolite Y, ZSM-5, MCM 22, MCM 56, or any mixture thereof.

11. The method of claim 1, wherein the reaction conditions comprise a temperature of from 700° C. to 1100° C.

12. The method of claim 1, wherein the reaction conditions comprise the presence of less than 1000 ppm weight of molecular oxygen with respect to the total weight of the hydrocarbon feed, the oxide of sulfur oxygen transfer reagent, and the molecular oxygen; and wherein at least a portion of the oxide of sulfur oxygen transfer reagent is reduced to produce the reduced sulfur oxygen transfer reagent.

13. The method of claim 1, wherein the reaction conditions comprise providing a source of molecular oxygen in an amount greater than 1000 ppm weight with respect to the total weight of the hydrocarbon feed, the oxide of sulfur oxygen transfer reagent, and the molecular oxygen.

14. The method of claim 1, wherein the oxide of sulfur oxygen transfer reagent further comprises at least one promotor comprising at least one of Mn, Fe, Co, Cu, V, Nb, Ta, Cr, Mo, W, vanadium, or any mixture thereof.

15. The method of claim 1, wherein step b) oxidatively dehydrogenating the hydrocarbon feed proceeds according to the reaction:

$$zCnH_{2n+2-2\beta}+(z-1+\delta)\text{“O”}\rightarrow C_{(z\times n)}H_{2(z\times n)+2-2\beta-2\delta}+(z-1+\delta)H_2O$$

wherein: z=the number of reactant molecules; n=the number of atomic units in the reactant molecule; β=the degree of unsaturation in the reactant molecule, where the value is zero for single bonds, and one for double bonds and molecular rings; δ=the change in the degree of unsaturation from the reactant molecule to the product molecule; and “O” is atomic oxygen; and wherein the atomic oxygen is supplied by the oxygen in the oxide of sulfur oxygen transfer reagent.

16. The method of claim 1, further comprising a step c) of contacting the oxide of sulfur oxygen transfer reagent with a gas-phase promoter comprising at least one of gas phase water, steam, $CO_2$, halide gases, hydrogen halides, or any mixture thereof.

17. The method of claim 16, wherein the step c) is performed at the same time as the step a).

18. The method of claim 1, wherein the step d) is performed at the same time as the step a).

19. The method of claim 1, wherein the gas comprising sulfur in d) comprises at least one of $SO_3$, $SO_2$, $H_2S$, elemental sulfur in any form, or any mixture thereof.

20. The method of claim 1, wherein the gas comprising sulfur in d) is a by-product of a hydrodesulfurization (HDS) unit.

21. The method of claim 1, further comprising:

e) removing a portion of the reduced sulfur oxygen transfer reagent;

f) contacting the portion of the reduced sulfur oxygen transfer reagent with a gas comprising at least one of molecular oxygen, a compound comprising sulfur, or a combination thereof to produce a regenerated oxide of sulfur oxygen transfer reagent; and g) feeding the regenerated oxide of sulfur oxygen transfer reagent to step a).

22. The method of claim 21, wherein the gas comprising sulfur in f) comprises at least one of $SO_2$, $H_2S$, elemental sulfur in any form, or any mixture thereof.

23. The method of claim 21, wherein the gas comprising sulfur in f) is a by-product of a hydrodesulfurization (HDS) unit.

24. The method of claim 1, wherein the oxide of sulfur oxygen transfer reagent is in the form of a mixture with an additional oxygen transfer reagent different from the oxide of sulfur oxygen transfer reagent.

* * * * *

UNITED STATES PATENT AND TRADEMARK OFFICE

CERTIFICATE OF CORRECTION

PATENT NO. : 12,023,655 B2
APPLICATION NO. : 18/108810
DATED : July 2, 2024
INVENTOR(S) : John A. Sofranko It is certified that error appears in the above-identified patent and that said Letters Patent is hereby corrected as shown below:

In the Claims

Column 16, Claim 1, Line 10:
d) contacting the oxide of sulfur oxygen transfer reagent with gas phase sulfur.
Should read:
c) contacting the oxide of sulfur oxygen transfer reagent with gas phase sulfur.

Signed and Sealed this
Thirteenth Day of August, 2024

Katherine Kelly Vidal

Katherine Kelly Vidal
*Director of the United States Patent and Trademark Office*